United States Patent [19]

Mohrs et al.

[11] Patent Number: 5,192,771

[45] Date of Patent: Mar. 9, 1993

[54] (QUINOLIN-2-YL-METHOXY)PHENYLA-CETIC ACID DERIVATIVES CONTAINING CYCLIC SUBSTITUENTS

[75] Inventors: Klaus Mohrs, Wuppertal; Siegfried Raddatz; Romanis Fruchtmann, both of Cologne; Christian Kohlsdorfer, Erftstadt; Reiner Müller-Peddinghaus; Pia Theisen-Popp, both of Bergisch-Gladbach, all of Fed. Rep. of Germany

[73] Assignee: Bayer Aktiengesellschaft, Leverkusen, Fed. Rep. of Germany

[21] Appl. No.: 561,038

[22] Filed: Aug. 1, 1990

[30] Foreign Application Priority Data

Aug. 24, 1989 [DE] Fed. Rep. of Germany ....... 3927930

[51] Int. Cl.$^5$ .................. A01N 43/42; C07D 215/12; C07D 214/14
[52] U.S. Cl. .................................. 514/311; 514/312; 514/314; 546/153; 546/154; 546/155; 546/156; 546/168; 546/170; 546/173; 546/174
[58] Field of Search ............... 546/174, 173, 153, 154, 546/155, 156, 168, 170; 514/314, 311, 312

[56] References Cited

U.S. PATENT DOCUMENTS 4,769,461 9/1988 Musser et al. ..................... 546/152
4,974,626 5/1990 Mohrs et al. ..................... 546/174

FOREIGN PATENT DOCUMENTS 0181568 5/1986 European Pat. Off. .
0200101 11/1986 European Pat. Off. .
0318093 5/1989 European Pat. Off. .
0344519 6/1989 European Pat. Off. .

*Primary Examiner*—Alan L. Rotman
*Assistant Examiner*—Raymond Covington
*Attorney, Agent, or Firm*—Sprung Horn Kramer & Wood

[57] ABSTRACT

For inhibiting lipoxygenzce, (quinolin-2-yl-methoxy) phenylacetic acid derivatives containing cyclic substituents of the formula

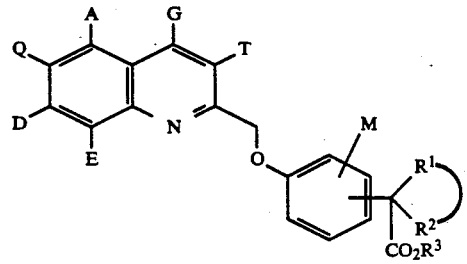

in which
A, Q, D, E, G, T and M are hydrogen or various radicals,
$R^3$ is halogen or an alkyl or phenyl radical, and
$R^1$ and $R^2$ complete a carbocyclic ring which may be substituted and/or fused to another ring,
and salts thereof.

11 Claims, No Drawings

(QUINOLIN-2-YL-METHOXY)PHENYLACETIC ACID DERIVATIVES CONTAINING CYCLIC SUBSTITUENTS

The invention relates to (quinolin-2-yl-methoxy)-phenylacetic acid derivatives containing cyclic substituents, processes for their preparation and their use in medicaments.

Meta-substituted 3-(quinolin-2-yl-methoxy)phenylacetic acids and 2-[3-(quinolin-2-yl-methoxy)phenyl]propionic acids and esters thereof are described in EP-A2 181,568. It is furthermore known that substituted (quinolin-2-yl-methoxy)phenyl derivatives have an anti-inflammatory and antiallergic action (compare EP-A3 110,405).

New (quinolin-2-yl-methoxy)phenylacetic acid derivatives containing cyclic substituents, of the general formula (I),

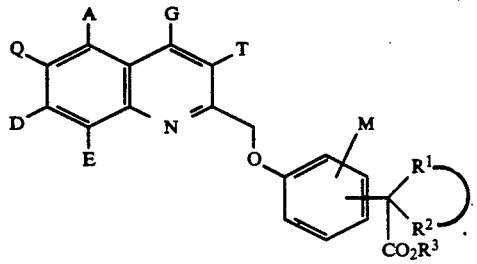

in which
A, B, D, E, G, K and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or
represent aryl having 6 to 10 carbon atoms, which is optionally substituted by halogen, nitro, cyano or by straight-chain or branched alkyl or alkoxy having up to 8 carbon atoms, $R^1$ and $R^2$, together with the carbon atom, form a 4- to 8-membered, saturated or unsaturated carbocyclic ring, which is optionally substituted by up to 3 identical or different substituents from the group comprising straight-chain or branched alkyl or alkoxy having in each case up to 8 carbon atoms, halogen, hydroxyl and aryl having 6 to 10 carbon atoms, or $R^1$ and $R^2$, together with the carbon atom, represent a radical of the formula

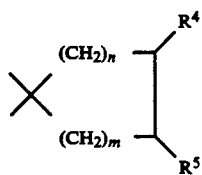

wherein
m and n are identical or different and denote the number 0, 1, 2, 3 or 4, and
$R^4$ and $R^5$ together complete an aryl radical having 6 to 10 carbon atoms or a 5- to 7-membered saturated or unsaturated heterocyclic radical having up to 3 heteroatoms from the series comprising nitrogen, sulphur or oxygen, which are optionally substituted by straight-chain or branched alkyl or alkoxy having in each case up to 8 carbon atoms, halogen or aryl having 6 to 10 carbon atoms, and $R^3$- represents hydrogen, straight-chain or branched alkyl having up to 8 carbon atoms or phenyl, and salts thereof, have now been found.

Physiologically acceptable salts are preferred in the context of the present invention Physiologically acceptable salts of the (quinolin-2-yl-methoxy)phenylacetic acid derivatives containing cyclic substituents can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are furthermore salts of monovalent metals, such as alkali metals, and the ammonium salts. Sodium, potassium and ammonium salts are preferred.

Preferred compounds of the general formula (I) are those
in which
A, Q, D, E, G, T and M are identical or different and represent hydrogen, fluorine, chlorine, trifluoromethoxy or carboxyl,
represent straight-chain or branched alkyl having up to 8 carbon atoms, which is optionally substituted by hydroxyl, fluorine, chlorine or bromine,
represent straight-chain or branched alkoxy or alkoxycarbonyl having up to 8 carbon atoms, or
represent phenyl, which is optionally substituted by fluorine, chlorine, bromine, nitro, cyano or by straight-chain or branched alkyl or alkoxy having up to 6 carbon atoms, $R^1$ and $R^2$, together with the carbon atom, represented cyclopropyl, cyclobutyl, cyclopentyl, cyclohexyl, cycloheptyl, cyclopentenyl, cyclohexenyl or cycloheptenyl, are optionally substituted by up to 2 identical or different substituents from the group comprising straight-chain or branched alkyl having up to 6 carbon atoms or phenyl, or $R^1$ and $R^2$, together with the carbon atom, represent a radical of the formula

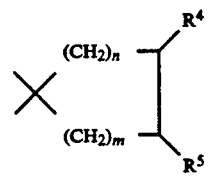

wherein
m and n are identical or different and denote the number 0, 1, 2 or 3,
$R^4$ and $R^5$ together complete phenyl, furanyl, thienyl, pyridyl or pyrryl, which are optionally substituted by straight-chain or branched alkyl or alkoxy having in each case up to 6 carbon atoms or fluorine, chlorine, bromine or phenyl, and R³ represents hydrogen, straight chain or branched alkyl having up to 8 carbon atoms or phenyl, and salts thereof.

Particularly preferred compounds of the general formula (I) are those in which

A, Q, D, E, G, T and M are identical or different and represent hydrogen, fluorine, chlorine, straight-chain or branched alkyl or alkoxy having up to 10 carbon atoms, R¹ and R² together with the carbon atom represent cyclopentyl, cyclopentenyl, cyclohexyl, cyclohexenyl, cycloheptyl or cycloheptenyl, which are optionally substituted by straight-chain or branched alkyl having up to 4 carbon atoms and/or phenyl, or R¹ and R² together with the carbon atom represent a radical of the formula

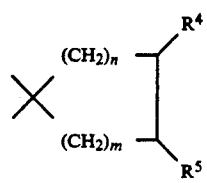

wherein m and n are identical or different and denote the number 1 or 2,

R⁴ and R⁵ phenyl, thienyl, pyridyl or pyrryl, which are optionally substituted by straight-chain or branched alkyl having up to 4 carbon atoms or phenyl, and R³ represents hydrogen or straight-chain or branched alkyl having up to 6 carbon atoms, and salts thereof.

Especially preferred compounds of the general formula (I) are those in which the quinolylmethoxy grouping on the phenyl is in the 4-position relative to the acetic acid radical containing a cyclic substituent.

A process for the preparation of the compounds according to the invention, of the general formula (I),

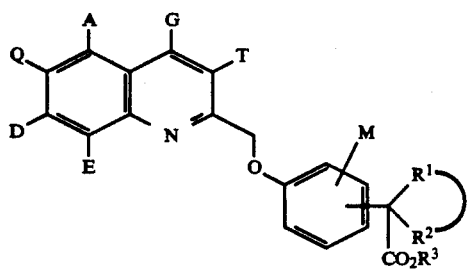

in which A, Q, D, E, G, T, M, R¹, R² and R³ have the abovementioned has furthermore been found, which is characterized in that the acidic CH compounds of the general formula (II)

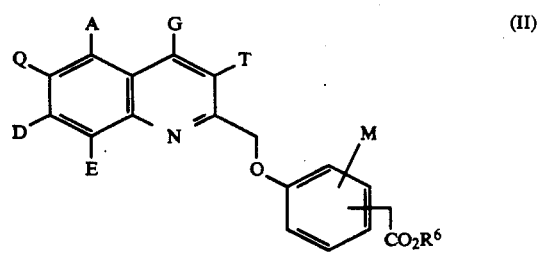

in which

A, Q, D, E, G, T and M have the abovementioned meanings, and

R⁶—has the abovementioned meaning of R³ but does not represent hydrogen, are reacted with dihalogeno compounds of the general formula (III)

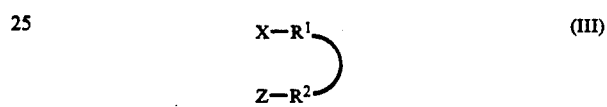

in which

R¹ and R² have the abovementioned meanings of R¹ and R², but are in the open-chain form, and X—represents halogen, in inert solvents, if appropriate in the presence of a base, and in the case of the acids the esters are then hydrolyzed.

The process can be illustrated by the following equation:

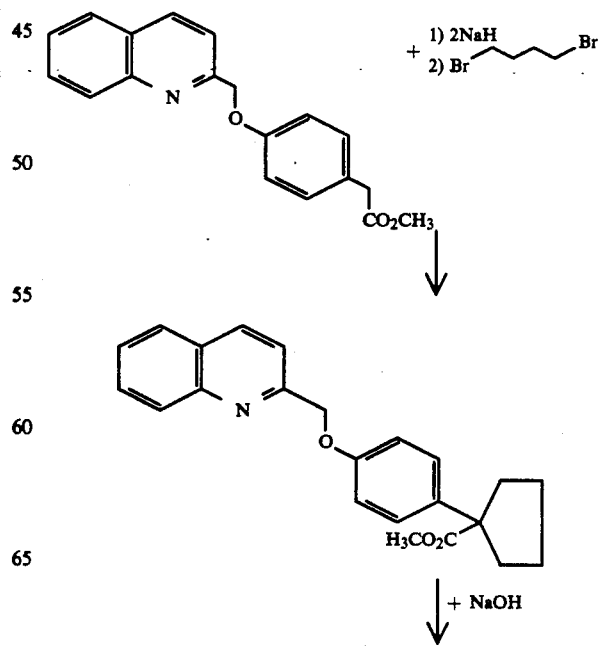

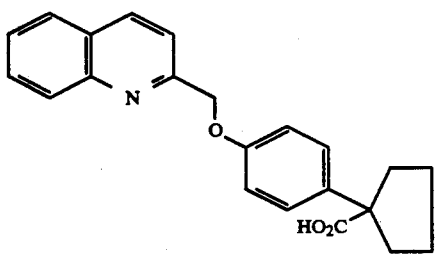

Suitable solvents for the process according to the invention are the customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is likewise possible to use mixtures of the solvents mentioned. Dimethylformamide is preferred.

Suitable bases are alkali metals, alkali metal hydrides, alkali metal amides, alkali metal alcoholates or organolithium compounds; alkali metal hydrides, such as sodium hydride or potassium hydride, are preferred.

The process according to the invention is in general carried out in a temperature range from $-10°$ C. to $+80°$ C., preferably at room temperature.

The process according to the invention is in general carried out under normal pressure. However, it is also possible for the process to be carried out under increased pressure or under reduced pressure (for example in a range from 0.5 to 5 bar).

In general, 2 to 3 xcles, preferably 2 moles of base are employed per mole of the acidic CH compounds of the general formula (II).

The dihalogeno compounds of the general formula (III) are known or can be prepared by a known method (compare Beilstein 1, 120; 1(32), 740; 5(3), 981).

Examples which may be mentioned are:

cis-1,4-dichloro-2-butene
1,2-bis(chloromethyl)-4,5-dimethylbenzene
3,4-bis(chloromethyl)-2,5-dimethyl-thiophene
1,4-dibromobutane
1,5-dibromobutane
1,5-dibromo-3-methyl-3-phenylpentane 1,5-dibromo-3-methyl-pentane It has proved to be advantageous to carry out the process described above under an inert gas.

The hydrolysis of the carboxylic acid esters is carried out by customary methods by treating the esters with customary bases in inert solvents, it being possible for the salts initially formed to be converted into the free carboxylic acids by treatment with acid.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide is particularly preferably employed.

Suitable solvents for the hydrolysis are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible for mixtures of the solvents mentioned to be employed.

The hydrolysis is in general carried out in a temperature range from $0°$ C. to $+100°$ C., preferably $+20°$ C. to $+80°$ C.

The hydrolysis is in general carried out under normal pressure However, it is also possible for the hydrolysis to be carried out under reduced pressure or under increased pressure (for example from 0.5 to 5 bar).

In carrying out the hydrolysis, the base is in general employed in an amount of 1 to 3 mols preferably 1 to 1.5 moles, per mole of the ester. Molar amounts of the reactants are particularly preferably used.

In carrying out the reaction, in the first step, the salts of the compounds according to the invention are formed as intermediate products, which can be isolated. The acids according to the invention are obtained by treatment of the salts with customary inorganic acids. These include, preferably, mineral acids, such as, for example, hydrochloric acid, hydrobromic acid, sulphuric acid or phosphoric acid. It has proved advantageous here in the preparation of the carboxylic acids for the basic reaction mixture of the hydrolysis to be acidified in a second step without isolation of the salts. The acids can then be isolated in the customary manner (compare GB 2,202,223 A1; US 4,769,461 A and EP 181, 568 A2).

The acidic CH compounds of the general formula (II) are known in some cases and can be prepared, for example, by etherifying compounds of the general formula (IV)

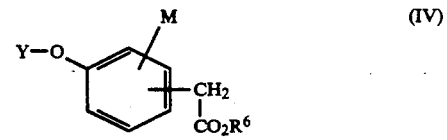

(IV)

in which

M and $R^6$ have the abovementioned meanings and

Y—represents a typical hydroxyl-protective group, such as, for example, benzyl or tert.-butyl, with halogenomethylquinolines of the formula (V)

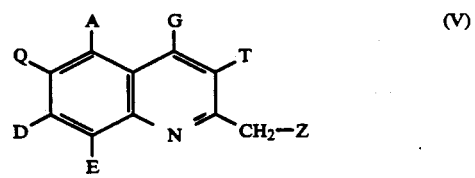

(V)

in which

A, Q, D, E, G and T have the abovementioned meanings and

Z—represents halogen, in inert solvents, if appropriate in the presence of a base, after eliminating the protective group Y by the customary method.

The protective groups are eliminated from the corresponding ethers by the customary method, for example by hydrogenolytic cleavage of the benzyl ether in the abovementioned inert solvents in the presence of a catalyst using hydrogen gas (compare also Th. Greene: "Protective Groups in Organic Synthesis", J. Wiley & Sons, 1981, New York).

The etherification can be carried out in inert organic solvents, if appropriate in the presence of a base.

Solvents for the etherification can be inert organic solvents which do not change under the reaction conditions. These include, preferably, ethers, such as, for example, dioxane, tetrahydrofuran or diethyl ether, halogenated hydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is also possible to employ mixtures of the solvents.

Bases which can be employed for the etherification are inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl(-$C_1$-$C_6$)amines), such as triethylamine, or heterocyclic compounds, such as pyridine, methylpiperidine, piperidine or morpholine.

It is also possible to employ alkali metals, such as sodium, and hydrides thereof, such as sodium hydride, as the bases.

The etherification is in general carried out in a temperature range from 0° C. to +150° C., preferably from +10° C. to +100° C.

The etherification is in general carried out under normal pressure. However, it is also possible for the process to be carried out under reduced pressure or increased pressure (for example in a range from 0.5 to 5 bar).

In general, 0.5 to 5, preferably 1 to 2 moles of halide are employed per mole of reactant. The base is in general employed in an amount of 0.5 to 5 moles preferably 1 to 3 moles, based on the halide.

The compounds of the general formulae (IV) and (V) are known per se or can be prepared by the customary method (compare Beilstein 10, 191; C. Ferri, Reaktionen der organischen Synthese [Reactions of Organic Synthesis], Georg Thieme Verlag, Stuttgart 1978; and Chem. Ber. 120, 649, 1987).

The compounds of the general formula (I) according to the invention surprisingly exhibit a high in vitro activity as leucotriene synthesis inhibitors and a potent in vivo action following oral administration.

The (quinolin-2-yl-methoxy)phenylacetic acid derivatives, containing cyclic substituents, according to the invention can be employed as active compounds in medicaments. The substances can act as inhibitors of enzymatic reactions in the context of arachidonic acid metabolism, in particular of lipoxygenase.

They are thus preferably suitable for the treatment and prevention of diseases of the respiratory tract, such as allergies/asthma, bronchitis, emphysema, shock lung, pulmonary hypertension, inflammations/rheumatism and oedemas, thromboses and thromboembolisms, ischaemias (peripheral, cardiac and cerebral disturbances in circulation), cardiac and cerebral infarctions, disturbances in cardiac rhythm, angina pectoris, arteriosclerosis in cases of tissue transplants, dermatoses, such as psoriasis, inflammatory dermatoses, for example eczema, Dermatophytes infection, infections of the skin by bacteria and metastases, and for cytoprotection in the gastrointestinal tract.

The (quinolin-2-yl-methoxy)phenylacetic acid derivatives, containing cyclic substituents, according to the invention can be used both in human medicine and in veterinary medicine.

The pharmacological action data of the substances according to the invention are determined by the following method:

The release of leucotriene $B_4$(LTB$_4$) on polymorphonuclear rat leukocytes (PMN) following addition of substances and Ca ionophore by means of reverse phase HPLC in accordance with the method of Borgeat, P. et al., Proc. Nat. Acad. Sci. 76, 2148–2152 (1979), was determined as a measure of the lipoxygenase inhibition. The in vivo activity of the compounds was demonstrated with the mouse ear inflammation model in accordance with the method of Young, J. M. et al., J. of Investigative Dermatology 82, 367–371, (1984).

The new active compounds can be converted in a manner which is known per se into the customary formulations, such as tablets, capsules, dragees, pills, granules, aerosols, syrups, emulsions, suspensions and solutions, using inert non-toxic, pharmaceutically suitable excipients or solvents. The therapeutically active compound here should in each case be present in the formulation in a concentration of about 0.5 to 90% by weight, preferably 10 to 70% by weight, that is to say in amounts which are sufficient to achieve the stated dosage range.

The formulations are prepared, for example, by extending the active compounds with solvents and/or excipients, if appropriate using emulsifying agents and/or dispersing agents, and in the case where water is used as the diluent, for example, it being possible for organic solvents to be used if appropriate as auxiliary solvents.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as natural rock powders (for example kaolins, aluminas, talc and chalk), synthetic rock powders (for example highly-disperse silica and silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

The administration can take place in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatin and the like. Lubricants, such as magnesium stearate, sodium lauryl sulphonate and talc, can furthermore be co-used for tablet-making. In the case of aqueous suspensions and/or elixirs intended for oral uses, various flavor-improving agents or dyestuffs, in addition to the abovementioned auxiliaries, can be added to the active compounds.

In the case of parenteral use, solutions of the active compounds can be employed, using suitable liquid excipients.

In general, it has proved advantageous to administer amounts of 0.01 to 10 mg/kg, preferably about 0.01 to 5 mg/kg of body weight, in the case of intravenous administration in order to achieve effective results. In the case of oral administration, the dosage is in general about 0.1 to 200 mg/kg, preferably 1 to 100 mg/kg of body weight.

Nevertheless, it may at times be necessary to deviate from the amounts mentioned, and in particular as a function of the body weight or nature of the administration route, of the individual behavior towards the medicament and of the nature of its formulation and the time or interval at which administration takes place. Thus in some cases it may suffice to manage with less than the abovementioned minimum amount, whereas in other cases the upper limit mentioned must be exceeded. Where relatively large amounts are administered, it may be advisable to divide these into several individual doses over the day.

STARTING COMPOUND

Example I

Methyl 4-(quinolin-2-yl-methoxy)phenylacetate

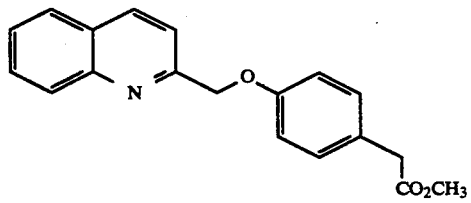

200 g (1.2 mol) of methyl 4-hydroxyphenyl acetate and 166 g (1.2 mol) of potassium carbonate are stirred in 2 l of dimethylformamide at 25° C. for 1 hour. After addition of 214 g (1.2 mol) of 2-chloromethylquinoline, the mixture is heated at 50° C. for 15 hours. After concentrating in vacuo, the residue is partitioned between water and ethyl acetate and the organic phase is dried over sodium sulphate and concentrated. The product which remains is recrystallized from methanol. Yield: 293 g (79 % of theory).

Melting point: 71°–73° C.

PREPARATION EXAMPLES (FORMULA I)

Example 1

Methyl 1-[4-(quinolin-2-yl-methoxy)phenyl]cyclopentanecarboxylate

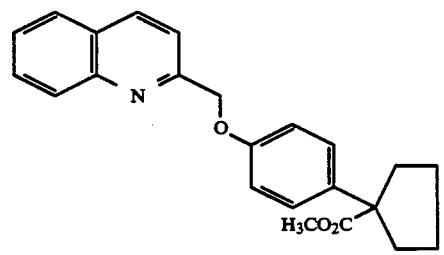

10 g (32.5 mmol) of the compound from Example I and 3.88 ml (32.5 mmol) of 1,4-dibromobutane are dissolved in 100 ml of dimethylformamide under an inert gas 10 and 1.95 g (65 mmol) of sodium hydride (80% strength) are added in portions. The mixture is stirred at room temperature for 15 hours and then poured on to 200 ml of ice-water and the product is filtered off with suction. The crude product is chromatographed on silica gel 60 using methylene chloride/methanol (100:2).

Yield: 5.47 g (46.6 % of theory).

Melting point 136° C. (methanol).

The compounds listed in Table 1 were prepared analogously to the procedure of Example 2.

TABLE 1

| Example No. | Ar*—[R1, R2]—CO2CH3 structure | Melting Point °C. | Yield % |
|---|---|---|---|
| 2 | Ar—cyclohexyl—H3CO2C | 85 | 35 |
| 3 | Ar—cyclobutyl—H3CO2C | 124–126 | 15 |
| 4 | Ar—C(C6H5)(CH3)-cyclohexyl—H3CO2C | 143 | 50 |
| 5 | Ar—(4-CH3-cyclohexyl)—H3CO2C | 148 | 28 |
| 6 | Ar—indanyl—H3CO2C | 142 | 7.5 |
| 7 | Ar—(5,6-dimethyl-indanyl)—H3CO2C | 177 | 25 |

TABLE 1-continued

| Example No. | Ar*—⟨R¹/R²⟩—CO₂CH₃ | Melting Point °C. | Yield % |
|---|---|---|---|
| 8 | 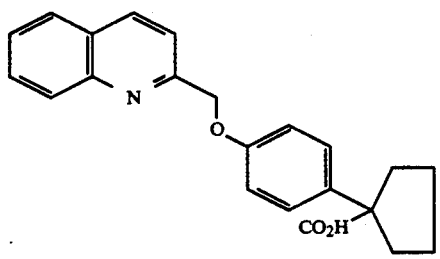 | 115–118 | 6.5 |

Ar* =

(quinoline-CH₂-O-p-tolyl structure)

Example 9
1-[4-(quinolin-2-yl-methoxy)phenyl]cyclopentanecarboxylic acid 5 g (13.8 mmol) of the compound from Example 1 are heated under reflux in 50 ml of dioxane and 15 ml of 2-normal sodium hydroxide solution for 15 hours. After cooling, the mixture is neutralized with hydrochloric acid and evaporated on a rotary evaporator. The product is stirred in water, filtered off with suction, dried and recrystallized from methanol.

Yield: 4.38 g (91.5 % of theory).
Melting point: 195° C. (methanol).

The compounds listed in Table 2 were prepared analogously to the procedure of Example 9.

TABLE 2

| Example No. | Ar*—⟨R¹/R²⟩—CO₂H | Melting Point °C. | Yield % |
|---|---|---|---|
| 10 | cyclohexane | 170 | 85 |
| 11 | cyclopentene | 194 | 97 |
| 12 | 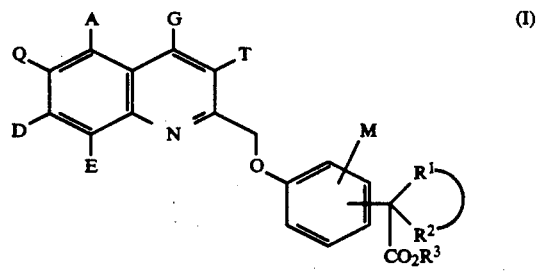 | 192 | 75 |
| 13 | indane | 207 | 72 |
| 14 | dimethyl-indane | >260 | 46 |
| 15 | dimethyl-thiophene-cyclopentane | 226 | 81 |

Ar* = (quinoline-CH₂-O-p-tolyl structure)

It is understood that the specification and examples are illustrative but not limitative of the present invention and that other embodiments within the spirit and scope of the invention will suggest themselves to those skilled in the art.

We claim:

1. A (quinolin-2-yl-methoxy)phenylacetic acid derivative containing a cyclic substituent of the formula $$\text{(I)}$$

in which
A, Q D, E, G, T and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or represent aryl having 6 to 10 carbon atoms, which is optionally substituted by halogen, nitro, cyano or by straight-chain or branched alkyl of the alkoxy having up to 8 carbon atoms, R¹ and R², together with the carbon atom, form a 4- to 8-membered, saturated or unsaturated carbocyclic ring, which is optionally substituted by up to 3 identical or different substituents from the group consisting of straight-chain or branched alkyl or alkoxy having in each case up to 8 carbon atoms, halogen, hydroxyl and aryl having 6 to 10 carbon atoms, or R¹ and R², together with the carbon atom, represent a radical of the formula

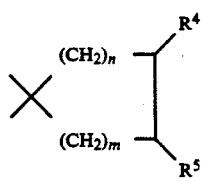

wherein
m and n are identical or different and denote the number 0, 1, 2, 3 or 4, and R⁴ and R⁵ together complete an aryl radical having 6 to 10 carbon atoms or which is optionally substituted by straight-chain or branched alkyl or alkoxy having in each case up to 8 carbon atoms, halogen or aryl having 6 to 10 carbon atoms, and R³—represents hydrogen, straight-chain or branched alkyl having up to 8 carbon atoms or phenyl, or a salt thereof.

2. A (quinolin-2-yl-methoxy)phenylacetic acid derivative containing a cyclic substituent or salt thereof according to claim 1,
wherein
A, Q, D, E, G, T and M are identical or different and represent hydrogen, fluorine, chlorine, trifluoromethoxy or carboxyl,
represent straight-chain or branched alkyl having up to 8 carbon atoms, which is optionally substituted by hydroxyl, fluorine, chlorine or bromine,
represent straight-chain or branched alkoxy or alkoxycarbonyl having up to 8 carbon atoms, or
represent phenyl, which is optionally substituted by fluorine, chlorine, bromine, nitro, cyano or by straight-chain or branched alkyl or alkoxy having up to 6 carbon atoms, R¹ and R², together with the carbon atom, represent cyclopropyl, cyclobutyl, byclopentyl, cyclohexyl, cycloheptyl, cyclopentenyl, cyclohexenyl or cycloheptenyl, is optionally substituted by up to 2 identical or different substituents from the group consisting of straight-chain or branched alkyl having up to 6 carbon atoms and phenyl, or R¹ and R², together with the carbon atom, represent a radical of the formula

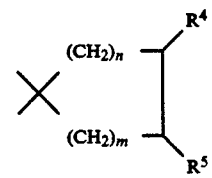

wherein
m and n are identical or different and denote the number 0, 1, 2 or 3,

R⁴ and R⁵ together complete phenyl, thienyl, which is optionally substituted by straight-chain or branched alkyl or alkoxy having in each case up to 6 carbon atoms, fluorine, chlorine, bromine or phenyl, and R³—represents hydrogen, straight chain or branched alkyl having up to 8 carbon atoms or phenyl 3. A (quinolin-2-yl-methoxy)phenylacetic acid derivative containing a cyclic substituent or salt thereof according to claim 1, wherein A, Q, D, E, F, T and M are identical or different and represent hydrogen, fluorine, chlorine, straight-chain or branched alkyl or alkoxy having up to 6 carbon atoms, R¹ and R², together with the carbon atom, represent cyclopentyl, cyclohexyl, cyclohexenyl, cycloheptyl or cycloheptenyl, which is optionally substituted by straight-chain or branched alkyl having up to 4 carbon atoms and/or phenyl, or R¹ and R², together with the carbon atom, represent a radical of the formula

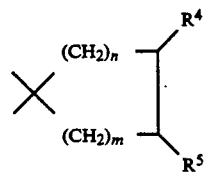

wherein
m and n are identical or different and denote the number 1 or 2,

R⁴ and R⁵ together complete phenyl, thienyl, which is optionally substituted by straight-chain or branched alkyl having up to 4 carbon atoms or phenyl, and R³ represents hydrogen or straight-chain or branched alkyl having up to 6 carbon atoms.

4. A compound according to claim 3, in which the quinolylmethoxy grouping on the phenyl is in the 4-position relative to the acetic acid radical containing a cyclic substituent.

5. A compound according to claim 1, wherein such compound is 1-[4-(quinolin-2-yl-methoxy)phenyl] cyclohexanecarboxylic acid of the formula

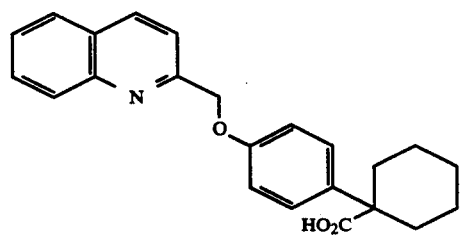

or a salt thereof.

6. A compound according to claim 1, wherein such compound is 1-[4-(quinolin-2-yl-methoxy)phenyl]-3-phenylcyclohexanecarboxylic acid of the formula

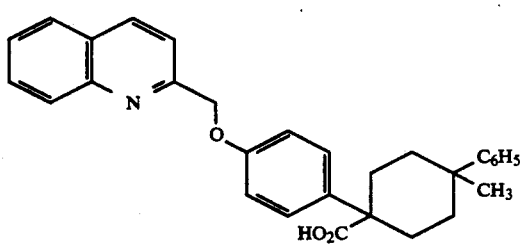

or a salt thereof.

7. A compound according to claim 1, wherein such compound is 1-[4-(quinolin-2-yl-methoxy)phenyl]-3,4-benzocylopentanecarboxylic acid of the formula

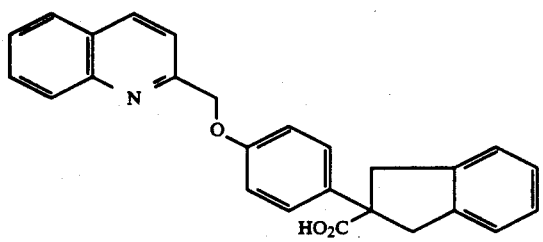

or a salt thereof

8. A compound according to claim 1, wherein such compound is 1-[4-(quinolin-2-yl-methoxy)phenyl]-3,4-(1,4-dimethyl-tetrahydrothien-3,4-yl)-cyclopentanecarboxylic acid of the formula

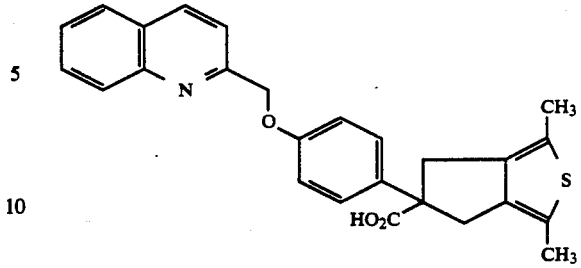

or a salt thereof

9. A lipoxygenase inhibiting composition comprising an amount effective therefor of a compound or salt thereof according to claim 1 and a pharmaceutically acceptable 10. A method of inhibiting lipoxygenase in a patient in need thereof which comprises administering to such patient an amount effective therefor of a compound or salt thereof according to claim 1.

11. The method according to claim 10, wherein such compound is

1-[4-(quinolin-2-yl-methoxy)phenyl] cyclohexanecarboxylic acid,
1-[4-(quinolin-2-yl-methoxy)phenyl]-3-phenylcyclohexanecarboxylic acid,
1-[4-(quinolin-2-yl-methoxy)phenyl]-3,4-benzocylopentanecarboxylic acid or
1-[4-(quinolin-2-yl-methoxy)phenyl]-3,4 (1,4-dimethyl-tetrahydrothien-3,4-yl-cyclopentanecarboxylic acid, or a salt thereof.

* * * * *

UNITED STATES PATENT AND TRADEMARK OFFICE
CERTIFICATE OF CORRECTION

PATENT NO. : 5,192,771
DATED : March 9, 1993
INVENTOR(S) : Mohrs et al

It is certified that error appears in the above-indentified patent and that said Letters Patent is hereby corrected as shown below:

On the title page: Item [56]

U.S. PATENT DOCUMENTS: Delete " 4,974,626 " and substitute -- 4,929,626 --

Col. 1, line 33    After " A " delete " B " and substitute -- Q --, after " G " delete " K " and substitute -- T --

Col. 13, line 28    After " or " insert -- thiophene --

Col. 13, line 54    Before " is " insert -- which --

Col. 14, line 15    Delete " F " and substitute -- G --

Col. 16, line 18    After " acceptable " insert -- diluent --

Signed and Sealed this

Sixth Day of September, 1994

BRUCE LEHMAN

Attest:

Attesting Officer    Commissioner of Patents and Trademarks